United States Patent [19]

Bridge

[11] Patent Number: 5,159,114
[45] Date of Patent: Oct. 27, 1992

[54] ACAT INHIBITORY BENZANILIDES

[75] Inventor: Andrew W. Bridge, Dagenham, England

[73] Assignee: Rhone-Poulenc Sante, France

[21] Appl. No.: 742,493

[22] Filed: Aug. 5, 1991

Related U.S. Application Data

[63] Continuation of Ser. No. 588,865, Sep. 27, 1990, abandoned.

[30] Foreign Application Priority Data

Sep. 27, 1989 [GB] United Kingdom .............. 8921792.1

[51] Int. Cl.$^5$ .................... C07C 235/38; C07C 237/52
[52] U.S. Cl. .................................... 564/154; 564/153; 564/157; 564/158
[58] Field of Search ............... 564/157, 158, 154, 153; 514/616

[56] References Cited

U.S. PATENT DOCUMENTS 4,002,655  1/1977  Hawkins .............................. 564/157
4,927,928  5/1990  Shroot et al. ....................... 564/158

OTHER PUBLICATIONS

Chem. Abs.-99 (7): 53390c, "Benzamides" Chugai Pharmaceutical Co., Ltd.

E. E. Largis, et al., CL 277,082: A novel inhibitor of ACAT-catalyzed cholesterol esterification and cholesterol absorption, Journal of Lipid Research, vol. 30, (May 1989), 681.

F. P. Bell, Arterial Cholesterol Esterification By Acyl-CoA-Cholesterol Acyltransferase: Its Possible Significance in Atherogenesis and Its Inhibition By Drugs, Pharmacological Control of Hyperlipidaemia, (1986), 409–422, J. R. Prous Science Publishers, S. A.

D. H. Blankenhorn, et al., Beneficial Effects of Combined Colestipol-Niacin Therapy on Coronary Atherosclerosis and Coronary Venous Bypass Grafts, JAMA, vol. 257, No. 23, (1987), 3233–3240.

E. R. Passamani, JAMA, Cholesterol Reduction in Coronary Artery Bypass Patients, JAMA, vol. 257, No. 23, (1987), 3271.

K. W. Walton, et al., Atherosclerosis in Vascular Grafts for Peripheral Vascular Disease, Atherosclerosis, 54, (1985), 49–63.

Primary Examiner—Marianne M. Cintins
Assistant Examiner—John Peabody
Attorney, Agent, or Firm—Morgan & Finnegan

[57] ABSTRACT

Benzanilide derivatives of the formula:

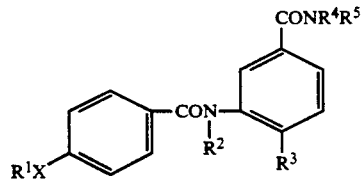

wherein
$R^1$ is alkyl optionally containing double or triple bonds, and optionally interrupted by one or more hetero atoms; $R^2$ is hydrogen, methyl, or ethyl;
$R^3$ is halogen, alkyl, —OY, —SY, or dimethylamino;
$R^4$ and $R^5$ are hydrogen, alkyl optionally containing double or triple bonds, or —(CH$_2$)$_m$—Z, wherein: Z is —OCH$_3$, —SCH$_3$, —N(CH$_3$)$_2$ or alkanoylamino, and m is 2, 3 or 4;
X is oxygen, —OCH$_2$—, —S—, —SCH$_2$— or —NR$^6$—;
$R^6$ is hydrogen, methyl, ethyl, or acyl; and
Y is alkyl; are useful as anti-atherosclerotic agents.

10 Claims, No Drawings

ACAT INHIBITORY BENZANILIDES

This is a continuation of co-pending application Ser. No. 07/588,865, filed on Sep. 27, 1990, and now abandoned.

FIELD OF THE INVENTION

This invention relates to new, therapeutically useful benzanilide derivatives, to a process for their production, to pharmaceutical compositions containing them, and methods for their use.

DESCRIPTION OF THE INVENTION

The new benzanilide derivatives of the present invention are the compounds of formula I, hereinafter depicted, wherein;

$R^1$ is a straight- or branched-chain alkyl group containing from 4 to 18 carbon atoms, optionally containing one or more carbon-carbon double or triple bonds, and optionally interrupted by one or more hetero atoms, e.g. oxygen, sulphur or nitrogen atoms;

$R^2$ is hydrogen, methyl, or ethyl;

$R^3$ is a halogen, e.g. chlorine or fluorine, atom or a straight- or branched-chain alkyl group of 1 to 5 carbon atoms, or a group of formula —OY or —SO$_n$Y, or is the dimethylamino group;

$R^4$ and $R^5$ are each independently hydrogen, a straight- or branched-chain alkyl group of up to 6 carbon atoms, optionally containing one or more carbon-carbon double or triple bonds, or a group of formula —(CH$_2$)$_m$—Z, wherein:

(i) Z is a group of formula —OCH$_3$, —SO$_q$CH$_3$ or —N(CH$_3$)$_2$ or an alkanoylamino group containing up to 3 carbon atoms, e.g. acetylamino, and m is 2, 3 or 4; or (ii) Z is a heterocyclyl group, preferably containing from 5 to 8 atoms in the ring, including at least one atom selected from nitrogen, oxygen and sulphur, and optionally carrying one or more substituents, for example alkyl groups containing from 1 to 4 carbon atoms, and m is 0, 1, 2, 3 or 4;

X is an oxygen atom or a group of formula —OCH$_2$—, —SO$_p$—, —SO$_p$CH$_2$— or —NR$^6$—;

$R^6$ is hydrogen, methyl, or ethyl, or an acyl group, for example an alkanoyl group of 2 to 4 carbon atoms optionally substituted by, for example, one or more halogen atoms;

Y is a straight- or branched-chain alkyl group of 1 to 4 carbon atoms; and n, p and q are each independently 0, 1, or 2

Heterocyclyl groups within the definition of Z are, for example, pyridyl, furyl, thiadiazolyl, morpholinyl, piperidinyl, isothiazolyl or pyrrolidinyl, optionally carrying 1 or 2 methyl or ethyl groups.

Preferred compounds according to the invention exhibit one or more of the following features—

(1) $R^1$ is an alkyl group preferably of 5 to 16, more preferably of 9 to 12, especially of 9 or 10, carbon atoms;

(2) $R^2$ is hydrogen;

(3) $R^3$ is methyl, methoxy, methylthio or ethylthio;

(4) $R^4$ is hydrogen;

(5) $R^5$ is either:

(i) an alkyl group of 1 to 5 carbon atoms and is more preferably butyl; or (ii) a group of formula —(CH$_2$)$_m$—Z, wherein m is 3 or, more preferably, 2 and Z is a methoxy or methylthio group; and/or (6) X is an oxygen or sulphur atom;

the other symbols being as hereinbefore defined.

Important compounds according to the invention include:

A  N-[2-methylthio-5-(2-methoxyethylaminocarbonyl)]-phenyl-4-decyloxybenzamide;

B  N-(2-methylthio-5-butylaminocarbonyl)phenyl-4-decyloxybenzamide;

C  N-[2-methylthio-5-(2-methylthioethylaminocarbonyl)]phenyl-4-decyloxybenzamide;

D  N-[2-methylthio-5-(2-methylthioethylaminocarbonyl)]phenyl-4-(decylthio)benzamide;

E  N-[2-methoxy-5-(2-methylthioethylaminocarbonyl)]-phenyl-4-decyloxybenzamide;

F  N-[2-methoxy-5-(2-methylthioethylaminocarbonyl)]-phenyl-4-nonyloxybenzamide;

G  N-(2-methoxy-5-butylaminocarbonyl)phenyl-4-(decylthio)benzamide;

H  N-butyl-4-methyl-3-[4-(3,6,9-trioxadecyloxybenzamido)]benzamide;

I  3-[4-(N-decyl)trifluoroacetamido]benzamido-4-methoxy-N-(2methylthioethyl)benzamide; and J  3-(4-decylaminobenzamido)-4-methoxy-N-(2-methylthioethyl)benzamide.

The letters A to J are allocated to compounds for easy reference later in this specification.

The compounds according to the invention are inhibitors of acyl coenzyme-A:cholesterol-O-acyl transferase (ACAT;EC 2.3.1.26). They are therefore of value as anti-atherosclerotic agents and have utility in the treatment of atherosclerosis, hyperlipidaemia, cholesterol ester storage disease and atheroma in vein grafts.

In assays performed in vitro, microsomes (prepared from the livers of rats fed a diet supplemented with 0.5% w/w cholesterol and 0.25% w/w cholic acid for 7 days) were incubated with radiolabelled oleoyl-CoA in the presence of compounds according to the invention at a concentration of 1 µg/ml. The degree of ACAT inhibition produced is shown in Table 1.

In in-vivo tests, using rats fed on a similar diet to that above and further supplemented by 0.03% w/w of test compound, compounds according to the invention inhibited increases in plasma cholesterol concentrations, measured after 3 days, relative to control animals fed on the cholesterol supplemented diet without the drug, as shown in Table 1.

TABLE 1

| Compound | In-vitro % Inhibition | In-vivo % Inhibition |
| --- | --- | --- |
| A | 82 | 100 |
| B | 94 | 92 |
| C | 98 | 91 |
| D | 94 | 100 |
| E | 83 | |
| F | 87 | |
| G | 91 | |

The compounds of formula I, and their intermediates, may be prepared by the application or adaptation of known methods, by which is meant methods used heretofore or described in the literature.

According to a feature of the present invention, compounds of formula I are prepared by the reaction of an aniline of general formula II hereinafter depicted with a compound of general formula III hereinafter depicted, wherein $R^1$, $R^2$, $R^3$, $R^4$, $R^5$ and X are as hereinbefore defined and $Z^1$ is a halogen, for example chlorine, atom or an alkoxycarbonyloxy, for example methoxycarbonyloxy or ethoxycarbonyloxy, group, or with a corresponding anhydride of general formula IV hereinafter depicted, wherein $R^1$ and X are as hereinbefore defined.

When $Z^1$ is halogen the reaction may be performed in the presence of a suitable base, such as a tertiary amine, e.g. triethylamine.

In each instance the reaction may be carried out in a suitable solvent, e.g. dichloromethane, optionally with heating.

As a further feature of the invention, compounds of formula I are prepared by the interconversion of other compounds of formula I.

For example, (i) compounds of general formula I wherein $R^2$ and $R^4$ are other than a hydrogen atom, $R^1$, $R^3$, $R^5$ and X being as hereinbefore defined, may be prepared from the corresponding compounds of formula I wherein $R^2$ and/or $R^4$ is/are hydrogen by the application or adaptation of known methods of alkylation, for example by using an alkyl halide in the presence of a base such as powdered sodium hydroxide preferably with potassium carbonate, in a solvent such as toluene, in the presence of a phase-transfer catalyst, such as a tetrabutylammonium salt (e.g. the hydrogen sulphate);

(ii) compounds of formula I wherein at least one of n, p and q is zero may be converted into a compound of formula I wherein n, p and/or q is greater than in the starting material, the other symbols being as hereinbefore defined, by the application or adaptation of known methods of oxidation of thio and/or sulphinyl groups to sulphinyl and/or sulphonyl groups, for example by using a percarboxylic acid (e.g. m-chloroperbenzoic acid), in an inert solvent, such as dichloromethane, at or below room temperature, or by using sodium perborate in acetic acid at about 50° to 55° C.; and (iii) compounds of formula I wherein X represents a group —$NR^6$— wherein $R^6$ represents an acyl group, and/or Z represents an alkanoylamino group, the other symbols being as hereinbefore defined, may be converted to the corresponding compounds of formula I wherein $R^6$ represents a hydrogen atom and/or Z represents an amino group by selective hydrolysis by the application or adaptation of known methods, for example using a dilute sodium hydroxide solution in aqueous ethanol, at or near room temperature.

Compounds of formula I can be purified by the usual physical means, for example by crystallization or chromatography.

Compounds of general formulae II, III and IV may be prepared by known methods.

Benzanilide compounds of general formula I wherein $R^1$ is a straight- or branched-chain alkyl or alkenyl group of 4 to 18 carbon atoms; $R^3$ is a straight- or branched-chain alkyl group of 1 to 5 carbon atoms, or a group of formula —OY or —$SO_nY$, or is the dimethylamino group; $R^4$ and $R^5$ are as hereinbefore defined except that Z is other than alkanoylamino, and $R^2$, X, $R^6$, Y, n, p and q are as hereinbefore defined constitute a feature of the present invention.

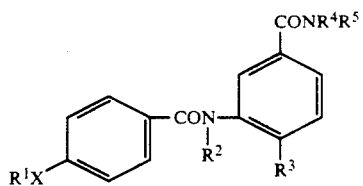

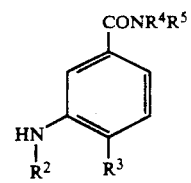

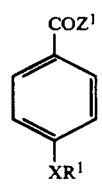

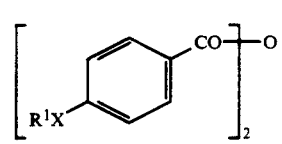

EXAMPLES

The following Examples illustrate the preparation of the compounds according to the invention and the Reference Examples illustrate the preparation of the intermediates.

Example 1

Compound A

A solution of 4-decyloxybenzoic acid (1.89 g) in thionyl chloride (18 ml) was heated at reflux for 3 hours. Excess thionyl chloride was removed under reduced pressure. The residue of 4-decyloxybenzoyl chloride in dichloromethane (20 ml) was added dropwise over 10 minutes to a stirred solution of N-(2-methoxyethyl)-4-methylthio-3-aminobenzamide (1.5 g) in dichloromethane (20 ml) and triethylamine (1 ml). The mixture was heated at reflux for 2 hours and was then concentrated under reduced pressure to leave a white solid. Recrystallization from ethyl acetate provided N-[2-methylthio-5-(2-methoxyethylaminocarbonyl)]phenyl-4-decyloxybenzamide (2.15 g) in the form of white needles, m.p. 112°–113° C. [Elemental analysis: C,66.8; H,7.95; N,5.48; S,6.4%; calculated: 67.17; H,8.05; N,5.59; S,6.4%].

Examples 2 to 7

Compounds B to G

By proceeding in a manner similar to that described in Example 1 but replacing the N-(2-methoxyethyl)-4-methylthio-3-aminobenzamide by N-butyl-4-methylthio-3-aminobenzamide, there was prepared N-(2-methylthio-5-butylaminocarbonyl)phenyl-4-decyloxybenzamide in the form of white crystals after recrystallization from aqueous ethanol and then from ethyl acetate, m.p. 131°–133° C. [Elemental analysis: C,69.9;

H,8.6; N,5.6; S,6.33%; calculated: C,69.88; H,8.43; N,5.62; S,6.43%].

By proceeding in a similar manner but replacing the N-(2-methoxyethyl)-4-methylthio-3-aminobenzamide by N-(2-methylthioethyl)-4-methylthio-3-aminobenzamide there was prepared N-[2-methylthio-5-(2-methylthioethylaminocarbonyl)]phenyl-4-decyloxybenzamide in the form of feathery, off-white needles after recrystallization from aqueous methanol, m.p. 120°–122° C. [Elemental analysis: C,65.3; H,7.9; N,5.1; S,12.0%; calculated: C,65.12; H,7.75; N,5.43; S,12.40%].

By proceeding in a similar manner but replacing the 4-decyloxybenzoic acid by 4-(decylthio)benzoic acid and by replacing the N-(2-methoxyethyl)-4-methylthio-3-aminobenzamide by N-(2-methylthioethyl)-4-methylthio-3-aminobenzamide there was prepared N-[2-methylthio-5-(2-methylthioethylaminocarbonyl)]phenyl-4-(decylthio)benzamide in the form of a white powder after crystallization from aqueous propan-2-ol and then from aqueous ethanol, m.p. 79°–86° C. [Elemental analysis: C,63.0; H,7.3; N,5.08; S,18.4%; calculated: C,63.12; H,7.56; N,5.25; S,18.05%].

By proceeding in a similar manner but replacing the N-(2-methoxyethyl)-4-methylthio-3-aminobenzamide by N-(2-methylthioethyl)-4-methoxy-3-aminobenzamide there was prepared N-[2-methoxy-5-(2-methylthioethylaminocarbonyl)]phenyl-4-decloxybenzamide in the form of white crystals after crystallization from aqueous methanol and then from ethanol, m.p. 134°–135° C. [Elemental analysis: C,66.9; H,8.1; N,5.5; S,6.4%; calculated: C,67.20; H,8.00; N,5.60; S,6.40%].

By proceeding in a similar manner but replacing the 4-decyloxybenzoic acid by 4-nonyloxybenzoic acid and by replacing N-(2-methoxyethyl)-4-methylthio-3-aminobenzamide by N-(2-methylthioethyl)-4-methyloxy-3-aminobenzamide there was prepared N-[2-methoxy-5-(2-methylthioethylaminocarbonyl)]phenyl-4-nonyloxybenzamide in the form of colorless crystals after crystallization from methanol and then from ethyl acetate, m.p. 132°–134° C. [Elemental analysis: C,66.8; H,8.0; N,5.66; S,6.8%: calculated: C,66.64; H,7.87; N,5.76; S,6.59%].

By proceeding in a similar manner but replacing the 4-decyloxybenzoic acid by 4-(decylthio)benzoic acid and by replacing the N-(2-methoxyethyl)-4-methylthio-3-aminobenzamide by N-butyl-4-methoxy-3-aminobenzamide there was prepared N-(2-methoxy-5-butylaminocarbonyl)phenyl-4-(decylthio)benzamide in the form of an off-white solid after crystallization from aqueous ethanol and then recrystallization from ethyl acetate, from methanol and finally from ethyl acetate again, m.p. 99°–101° C. [Elemental analysis: C,70.1; H,8.6; N,5.5; S,6.7%; calculated: C,69.88; H,8.43; N,5.62; S,6.42%].

Example 8

Compound H

A cold (0° C.) stirred solution of 4-(3,6,9-trioxadecyloxy)benzoic acid (2.84 g) and triethylamine (1.11 g) in dichloromethane (28 ml) was treated slowly with ethyl chloroformate (1.2 g) and the mixture was stirred at from 0° to 5° C. for 90 minutes. It was then treated with a solution of 3-amino-N-butyl-4-methylbenzamide (2.47 g) in dichloromethane (20 ml) and the mixture was stirred at the ambient temperature for 20 hours. The solvent was then removed and the mixture was treated with toluene (50 ml) and heated at 100° C. for 5 hours. It was then diluted with ethyl acetate (150 ml) and washed successively with water (1×50 ml), aqueous sodium hydroxide solution (2×50 ml; 1N), water (1×50 ml), hydrochloric acid (2×50 ml; 2N), and finally with brine (1×50 ml). The organic solution was then dried over magnesium sulphate and evaporated. The resulting residue was dissolved in hot ethyl acetate (50 ml) and this solution was treated with activated charcoal, filtered and diluted with diethyl ether. The crystals which formed were collected and dried, to give N-butyl-4-methyl-3-[4-(3,6,9-trioxadecyloxybenzamido)]benzamide (1.56 g) in the form of colorless plates, m.p. 102°–104° C. [Elemental analysis: C,65.8; H,7.7; N,6.07%; calculated: C,66.10; H,7.63; N,5.93%].

Example 9

Compound I

A stirred mixture of 3-amino-4-methoxy-N-(2-methylthioethyl)benzamide (2 g) and triethylamine in dichloromethane (20 ml) was treated slowly with 4-(N-decyl)trifluoroacetamidobenzoyl chloride (3.95 g) in dichloromethane (10 ml) at the ambient temperature and then it was stirred for 90 minutes. It was then washed successively with water (50 ml), hydrochloric acid (50 ml; 2N), and water (50 ml). The organic solution was then dried over magnesium sulphate and evaporated. The residue was recrystallized from a mixture of light petroleum (b.p. 40°–60° C.) and ethyl acetate, to give 3-[4-(N-decyl)trifluoroacetamido]benzamido-4-methoxy-N-(2-methylthioethyl)benzamide (2.0 g) in the form of a colorless solid, m.p. 135° C. [Elemental analysis: C,60.7; H,6.91; N,7.1; S,5.5%; calculated: C,60.48; H,6.77; N,7.05; S,5.38%].

Example 10

Compound J

A mixture of 3-[4-(N-decyl)trifluoroacetamido]benzamido-4-methoxy-N-(2-methylthioethyl)benzamide (1.0 g) and aqueous sodium hydroxide solution (2 ml; 2N) in ethanol (60 ml) was stirred at the ambient temperature for one hour. It was then treated with water (100 ml) and the resulting emulsion was extracted with ethyl acetate (100 ml). The extract was dried over magnesium sulphate and evaporated and the resulting residue was then triturated with light petroleum (b.p. 40°–60° C.) to give 3-(4-decylaminobenzamido)-4-methoxy-N-(2-methylthioethyl)benzamide (0.5 g), in the form of a colorless solid, m.p. 100°–104° C. [Elemental analysis: C,67.5; H,8.2; N,8.2; S,6.3%; calculated: C,67.29; H,8.27; N,8.4; S,6.42%].

Example 11

By carrying out processes similar to those described herein, more especially in the Examples and Reference Examples, there were prepared the following compounds:

N-butyl-4-methyl-3-(4-pentyloxybenzamido)benzamide, m.p. 163°–165° C. from aqueous ethanol;

N-butyl-4-methoxy-3-(4-pentyloxybenzamido)benzamide, m.p. 119°–121° C. from aqueous methanol;

N-(2-methylthioethyl)-4-methylthio-3-(4-pentyloxybenzamido)benzamide, m.p. 142°–143° C. from ethyl acetate;

4-methoxy-N-(2-methylthioethyl)-3-(4-pentyloxybenzamido)benzamide, m.p. 145°–147° C. from ethyl acetate;

N-butyl-4-methyl-3-(4-pent-4'-enyloxybenzamido)benzamide, m.p. 161°-163° C. from aqueous ethanol;

4-methoxy-3-(4-octyloxybenzamido)-N-pentylbenzamide, m.p. 116°-118° C. from isopropanol;

N-butyl-4-methylthio-3-(4-octyloxybenzamido)benzamide, m.p. 135°-136° C. from amyl acetate;

N-butyl-4-methylthio-3-(4-nonyloxybenzamido)benzamide, m.p. 135°-136° C. from aqueous ethanol;

N-(2-methoxyethyl)-4-methylthio-3-(4-nonyloxybenzamido)benzamide, m.p. 106°-108° C. from methanol;

4-methoxy-N-(3-methoxypropyl)-3-(4-nonyloxybenzamido)benzamide, m.p. 104°-106° C. from methanol;

N-(2-methylthioethyl)-4-methylthio-3-(4-nonyloxybenzamido)benzamide, m.p. 130°-132° C. from a mixture of light petroleum (b.p. 100°-120° C.) and ethanol;

N-butyl-3-(4-decyloxybenzamido)-4-methylbenzamide, m.p. 142°-144° C. from acetonitrile;

N-butyl-3-(4-decyloxybenzamido)-4-methoxybenzamide, m.p. 113°-115° C. from a mixture of diethyl ether and isopropanol;

N-butyl-3-(4-decyloxybenzamido)-4-methoxy-N-methylbenzamide, m.p. 75°-80° C. from light petroleum (b.p. 60°-80° C.);

3-(4-decyloxybenzamido)-N-(2-methoxyethyl)-4-methylbenzamide, m.p. 127°-129° C. from a mixture of ethanol and hexane;

3-(4-decyloxybenzamido)-N-(2-methoxyethyl)-4-methoxybenzamide, m.p. 103°-104° C. from diethyl ether;

3-(4-decyloxybenzamido)-N-(2-methoxyethyl)-4-propylbenzamide, m.p. 101°-103° C. from aqueous ethanol;

3-(4-decyloxybenzamido)-N-(2-methoxyethyl)-4-propoxybenzamide, m.p. 97°-99° C. from aqueous ethanol;

3-(4-decyloxybenzamido)-4-isopropoxy-N-(2-methoxyethyl)benzamide, m.p. 92°-94° C. from aqueous ethanol;

3-(4-decyloxybenzamido)-4-isopropyl-N-(2-methoxyethyl)benzamide, m.p. 124°-125° C. from amyl acetate;

3-(4-decyloxybenzamido)-4-methoxy-N-(3-methoxypropyl)benzamide, m.p. 105°-106° C. from a mixture of light petroleum (b.p. 60°-80° C.) and ethanol;

3-(4-decyloxybenzamido)-4-methoxy-N-(3-methylthiopropyl)benzamide, m.p. 131°-133° C. from a mixture of light petroleum (b.p. 80°-100° C.) and ethanol;

3-(4-decyloxybenzamido)-N-(2-methylthioethyl)-4-propylbenzamide, m.p. 105°-107° C. from aqueous ethanol;

3-(4-decyloxybenzamido)-N-(2-methylthioethyl)-4-propoxybenzamide, m.p. 120°-122° C. from aqueous ethanol;

3-(4-decyloxybenzamido)-4-methyl-N-(2-methylthioethyl)benzamide, m.p. 132°-134° C. from ethyl acetate;

3-(4-decyloxybenzamido)-4-isopropoxy-N-(2-methylthioethyl)benzamide, m.p. 98°-100° C. from aqueous ethanol;

3-(4-decyloxybenzamido)-4-isopropyl-N-(2-methylthioethyl)benzamide, m.p. 138°-140° C. from aqueous ethanol;

3-(4-decyloxybenzamido)-4-methoxy-N-(3-methylbutyl)benzamide, m.p. 118°-120° C. from ethanol;

3-(4-decyloxybenzamido)-4-methoxy-N-propylbenzamide, m.p. 116°-117° C. from aqueous ethanol;

3-(4-decyloxybenzamido)-4-methoxy-N-pentylbenzamide, m.p. 110°-111° C. from aqueous ethanol;

N-(2-methylthioethyl)-4-methylthio-3-(4-undecyloxybenzamido)benzamide, m.p. 108°-110° C. from isopropanol;

N-butyl-4-ethylthio-3-(4-undecyloxybenzamido)benzamide, m.p. 103°-105° C. from ethyl acetate;

N-butyl-4-methylthio-3-(4-undecyloxybenzamido)benzamide, m.p. 128°-130° C. from a mixture of light petroleum (b.p. 100°-120° C.) and ethanol;

N-(2-methoxyethyl)-4-methylthio-3-(4-undecyloxybenzamido)benzamide, m.p. 105°-107° C. from a mixture of light petroleum (b.p. 100°-120° C.) and ethanol;

3-(4-dodecyloxybenzamido)-N-(2-methoxyethyl)-4-methoxybenzamide, m.p. 108°-110° C. from cyclohexane;

N-butyl-3-(4-dodecyloxybenzamido)-4-(methylthio)benzamide, m.p. 130°-131° C. from toluene;

N-butyl-3-(4-dodecyloxybenzamido)-4-methoxybenzamide, m.p. 111°-113° C. from a mixture of light petroleum (b.p. 80°-100° C.) and methyl ethyl ketone;

N-butyl-3-(4-dodecyloxybenzamido)-4-(ethylthio)benzamide, m.p. 109°-111° C. from ethyl acetate;

N-butyl-3-(4-hexadecyloxybenzamido)-4-(methylthio)benzamide, m.p. 117°-118° C. from ethyl acetate;

3-(4-hexadecyloxybenzamido)-N-(2-methoxyethyl)-4-methylbenzamide, m.p. 126°-128° C. from a mixture of ethyl acetate and amyl acetate;

3-(4-hexadecyloxybenzamido)-N-(2-methoxyethyl)-4-methoxybenzamide, m.p. 109°-111° C. from ethyl acetate;

N-butyl-3-(4-hexadecyloxybenzamido)-4-methoxybenzamide, m.p. 109°-112° C. from butan-2-one;

N-(2-methoxyethyl)-4-methyl-3-[4-(3,6,9-trioxadecyloxybenzamido)]benzamide, m.p. 70°-72° C. from ethyl acetate;

N-(2-methoxyethyl)-4-methylthio-3-[4-(3,6,9-trioxadecyloxybenzamido)]benzamide, m.p. 108°-110° C. from ethyl acetate;

N-(2-methylthio)ethyl-4-methylthio-3-[4-(3,6,9-trioxadecyloxybenzamido)]benzamide, m.p. 94°-96° C. from ethyl acetate;

N-butyl-4-methylthio-3-[4-(3,6,9-trioxadecyloxybenzamido)]benzamide, m.p. 119°-121° C. from aqueous ethanol;

N-butyl-4-ethylthio-3-[4-(3,6,9-trioxadecyloxybenzamido)]benzamide, m.p. 109°-111° C. from aqueous ethanol;

N-butyl-4-methyl-3-(4-nonyloxymethylbenzamido)benzamide, m.p. 102°-104° C. from a mixture of ethyl acetate and diethyl ether;

N-butyl-4-methoxy-3-(4-nonyloxymethylbenzamido)benzamide, m.p. 102°-104° C. from aqueous ethanol;

N-(2-methoxyethyl)-4-methoxy-3-(4-nonyloxymethylbenzamido)benzamide, m.p. 77°-79° C. from a mixture of n-hexane and ethyl acetate;

3-[4-(decylthio)benzamido]-N-(2-methoxyethyl)-4-methylbenzamide, m.p. 128°-129° C. from isopropanol;

3-[4-(decylthio)benzamido]-N-(2-methoxyethyl)-4-propylbenzamide, m.p. 115°-117° C. from methanol;

3-[4-(decylthio)benzamido]-N-(2-methoxyethyl)-4-propoxybenzamide, m.p. 108°-110° C. from aqueous ethanol;

3-[4-(decylthio)benzamido]-4-isopropoxy-N-(2-methoxyethyl)benzamide, m.p. 88°-90° C. from methanol;

3-[4-(decylthio)benzamido]-4-isopropyl-N-(2-methoxyethyl)benzamide, m.p. 121°-122° C. from ethyl acetate;

3-[4-(decylthio)benzamido]-4-isopropoxy-N-(2-methylthioethyl)benzamide, m.p. 79°–81° C. from aqueous ethanol;

3-[4-(decylthio)benzamido]-N-(2-methylthioethyl)-4-propylbenzamide, m.p. 108°–110° C. from aqueous ethanol;

3-[4-(decylthio)benzamido]-N-(2-methylthioethyl)-4-propoxybenzamide, m.p. 101°–103° C. from light petroleum (b.p. 80°–100° C.);

3-[4-(decylthio)benzamido]-4-methoxy-N-(3-methylthiopropyl)benzamide, m.p. 118°–120° C. from methanol;

N-(2-methylthioethyl)-4-methylthio-3-[4-(octylthio)benzamido]benzamide, m.p. 92°–94° C. from t-butyl methyl ether;

N-butyl-4-methylthio-3-[4-(octylthio)benzamido]benzamide, m.p. 117°–120° C. from aqueous ethanol;

3-[4-(dodecylthio)benzamido]-4-methylthio-N-(2-methylthioethyl)benzamide, m.p. 86°–88° C. from aqueous ethanol;

N-butyl-3-[4-(dodecylthio)benzamido]-4-(methylthio)benzamide, m.p. 116°–118° C. from aqueous ethanol;

N-butyl-3-[4-(N-decyltrifluoroacetamido)benzamido]-4-(methylthio)benzamide, m.p. 168°–170° C. from ethyl acetate;

4-methoxy-N-(2-methylthioethyl)-3-[4-(N-octyltrifluoroacetamido)benzamido]benzamide, m.p. 136°–138° C. from ethyl acetate;

N-butyl-4-methylthio-3-[4-(N-octyltrifluoroacetamido)benzamido]benzamide, m.p. 181°–183° C. from ethyl acetate;

N-butyl-3-[4-(N-dodecyltrifluoroacetamido)benzmido]-4-(methylthio)benzamide, m.p. 163°–164° C. from ethyl acetate;

3-[4-(N-dodecyltrifluoroacetamido)benzamido]-4-methoxy-N-(2-methylthioethyl)benzamide, m.p. 114°–117° C. from a mixture of light petroleum (b.p. 60°–80° C.) and ethyl acetate;

N-butyl-3-(4-decylaminobenzamido)-4-(methylthio)benzamide, m.p. 150°–152° C. after trituration with light petroleum (b.p. 40°–60° C.);

N-butyl-3-(4-dodecylaminobenzamido)-4-(methylthio)benzamide, m.p. 148°–150° C. after trituration with light petroleum (b.p. 40°–60° C.);

3-(4-dodecylaminobenzamido)-4-methoxy-N-(2-methylthioethyl)benzamide m.p. 110°–112° C. after trituration with light petroleum (b.p. 40°–60° C.);

N-butyl-4-methylthio-3-(4-octylaminobenzamido)benzamide, m.p. 155°–157° C. from ethyl acetate;

4-methoxy-N-(2-methylthio)ethyl-3-(4-octylaminobenzamido)benzamide, m.p. 205°–210° C. from methanol, [Elemental analysis: C,61.1; H,7.6; N,8.1; S,6.50%; calculated for $C_{26}H_{37}N_3O_3S:HCl$: C,61.46; H,7.54; N,8.27; S,6.31%];

N-butyl-3-(4-dodecyloxy-N-methylbenzamido)-4-methoxybenzamide; m.p. indistinct after flash chromatography (using a mixture of dichloromethane and methanol 15:1 v/v as eluent);

N-butyl-3-(4-decyloxy-N-methylbenzamido)-4-methoxy-N-methylbenzamide, in the form of an oil after flash chromatography (using a mixture of dichloromethane and methanol 19:1 v/v as eluent);

N-butyl-3-(4-decylsulphonylbenzamido)-4-methoxybenzamide, m.p. 146°–148° C. from isopropanol;

N-(2-methylsulphonylethyl)-4-methylsulphonyl-3-(4-pentyloxybenzamido)benzamide, m.p. 168°–170° C. from aqueous ethanol;

4-methoxy-N-(2-methylsulphonylethyl)-3-(4-pentyloxybenzamido)benzamide, m.p. 130°–131° C. from ethanol;

3-(4-decyloxybenzamido)-4-methyl-N-(2-methylsulphonylethyl)benzamide, m.p. 134°–137° C. from toluene;

3-(4-decyloxybenzamido)-4-methyl-N-(2-methylsulphinylethyl)benzamide, m.p. 168°–169° C. from methanol;

3-(4-decyloxybenzamido)-4-methoxy-N-(2-methylsulphinylethyl)benzamide, m.p. 137°–138° C. from methyl ethyl ketone;

3-(4-decyloxybenzamido)-4-methoxy-N-(2-methylsulphonyl)ethylbenzamide, m.p. 124°–125° C. from ethanol;

3-(4-decyloxybenzamido)-N-(2-methoxyethyl)-4-methylsulphonylbenzamide, m.p. 95°–97° C. from diisopropyl ether;

N-butyl-3-(4-decyloxybenzamido)-4-methylsulphonylbenzamide, m.p. 121°–123° C. from ethanol;

N-butyl-3-(4-decyloxybenzamido)-4-methylsulphinylbenzamide, m.p. 130°–132° C. after flash chromatography (14:1 dichloromethane:methanol as eluent);

3-(4-decyloxybenzamido)-4-methylsulphonyl-N-(2-methylsulphonylethyl)benzamide, m.p. 149°–151° C. from ethyl acetate;

3-(4-decyloxybenzamido)-4-methoxy-N-(2-pyrid-4-ylethyl)benzamide, m.p. 123°–125° C. from ethyl acetate;

3-(4-decyloxybenzamido)-N-(4,6-dimethylpyrid-2-yl)-4-methoxybenzamide, m.p. 110°–112° C. from ethyl acetate;

3-(4-decyloxybenzamido)-N-(fur-2-ylmethyl)-4-methoxy-benzamide, m.p. 110°–111° C. from dichloromethane by trituration with diethyl ether;

3-(4-decyloxybenzamido)-4-methoxy-N-(5-methyl-1,3,4-thiadiazol-2-yl)benzamide, m.p. 210°–212° C. by trituration with dichloromethane;

3-(4-decyloxybenzamido)-4-methylthio-N-(5-methyl-1,3,4-thiadiazol-2-yl)benzamide, m.p. 226°–228° C. from dimethylformamide;

3-(4-decyloxybenzamido)-4-methoxy-N-(morpholin-4-yl)benzamide, m.p. 150°–152° C. from methanol;

3-(4-decyloxybenzamido)-4-methoxy-N-(4-methylpiperazin-1-yl)benzamide, m.p. 72°–74° C. after flash chromatography (9:1 dichloromethane:methanol as eluent);

3-(4-decyloxybenzamido)-4-methoxy-N-(pyrid-2-ylmethyl)benzamide, m.p. 124°–126° C. from toluene, [Elemental analysis: C,69.4; H,7.6; N,7.60; $H_2O$,3.8%; calculated for $C_{31}H_{39}N_3O_4:H_2O$: C,69.51; H,7.72; N,7.80; $H_2O$,3.4%];

3-(4-decyloxybenzamido)-4-methoxy-N-(piperidin-1-yl)ethyl)benzamide, m.p. 104°–106° C. from ethyl acetate after trituration with diethyl ether, [Elemental analysis: C,69.30; H,8.70; N,7.40% calculated for $C_{32}H_{47}N_3O_4:H_2O$: C,69.19; H,8.83; N,7.57%];

3-(4-decyloxybenzamido)-4-methoxy-N-(3-methylisothiazol-5-yl)benzamide, m.p. 240°–242° C. from ethyl acetate, [Elemental analysis: C,61.8; H,6.7; N,7.50; S,5.79%; calculated for $C_{29}H_{37}N_3O_4S$: $2H_2O$: C,62.25; H,7.33; N,7.51; S,5.72%];

3-(4-decyloxybenzamido)-N-(1-ethylpyrrolidin-2-ylmethyl)-4-methoxybenzamide, m.p. 165°–167° C. from ethyl acetate, [Elemental analysis: C,66.40; H, 8.40; Cl,6.20; N, 7.20%; calculated for $C_{32}H_{47}N_3O_4$: HCl: C,66.94; H, 8.43; Cl, 6.17; N, 7.32%];

3-(4-decyloxybenzamido)-4-ethoxy-N-methylbenzamide, m.p. 130°-132° C. from aqueous ethanol;

3-(4-decyloxybenzamido)-4-ethoxy-N-(2-methoxyethyl)benzamide, m.p. 117°-119° C. from ethyl acetate;

3-(4-decyloxybenzamido)-N-(2-dimethylaminoethyl)-4-(ethylthio)benzamide, m.p. 97°-99° C. from t-butyl methyl ether;

3-(4-decyloxybenzamido)-4-ethoxy-N-(3-methylbut-2-enyl)benzamide, m.p. 117°-118° C. from ethanol;

3-(4-decyloxybenzamido)-N-(2-dimethylaminoethyl)-4-ethoxybenzamide, m.p. 109°-111° C. from t-butyl methyl ether;

3-(4-decyloxybenzamido)-4-ethoxy-N-ethylbenzamide, m.p. 1.1°-133° C. from aqueous ethanol;

N-butyl-3-(4-decyloxybenzamido)-4-(ethylthio)benzamide, m.p. 115°-117° C. from diethyl ether;

N-butyl-3-(4-decyloxybenzamido)-4-ethoxybenzamide, m.p. 131°-133° C. from aqueous ethanol;

3-(4-decyloxybenzamido)-N-(3-dimethylaminopropyl)-4-ethoxybenzamide, m.p. 95°-97° C. from t-butyl methyl ether;

3-(4-decyloxybenzamido)-N-(3-dimethylaminopropyl)-4-(ethylthio)benzamide, m.p. 100°-101° C. from t-butyl methyl ether;

3-(4-decyloxybenzamido)-4-ethylthio-N-(2-methylthioethyl)benzamide, m.p. 105°-107° C. from aqueous ethanol;

3-(4-decyloxybenzamido)-N-ethyl-4-(ethylthio)benzamide, m.p. 115°-117° C. from ethyl acetate;

4-chloro-3-(4-decyloxybenzamido)-N-(3-methylbutyl)benzamide, m.p. 111°-113° C. from aqueous ethanol;

N-(2-acetamidoethyl)-3-(4-decyloxybenzamido)-4-(methylthio)benzamide, m.p. 181°-183° C. from aqueous ethanol;

3-(4-decyloxybenzamido)-4-fluoro-N-(2-methoxyethyl)benzamide, m.p. 140°-141° C. from a mixture of methanol and toluene;

3-(4-decyloxybenzamido)-N-(3-methylbut-2-enyl)-4-(methylthio)benzamide, m.p. 135°-136° C. from methanol;

4-chloro-3-(4-decyloxybenzamido)-N-(2-methylthioethyl)benzamide, m.p. 136°-137° C. from toluene;

N-butyl-4-chloro-3-(4-decyloxybenzamido)benzamide, m.p. 130°-131° C. from toluene;

N-butyl-3-(4-decyloxybenzamido)-4-fluorobenzamide, m.p. 133°-134° C. after chromatography on silica gel eluting with a mixture of dichloromethane and methanol;

N-butyl-3-(4-decyloxybenzamido)-4-dimethylaminobenzamide, m.p. 108°-109° C. after chromatography on silica gel eluting with a mixture of dichloromethane and ethyl acetate;

3-(4-decyloxybenzamido)-4-dimethylamino-N-(2-methylthioethyl)benzamide, m.p. 155°-158° C. in the form of the hydrochloride salt from acetone, [Elemental analysis: C,62.8; H,8.0; N,7.6; S,6.1; Cl,6.67%; calculated for $C_{29}H_{43}N_3O_3S \cdot HCl$: C,63.31; H,8.06; N,7.63; S,5.83; Cl,6.44%]; and 4-ethylthio-N-(3-methylthiopropyl)-3-(4-undecyloxybenzamido)benzamide, m.p. 102°-104° C. in the form of a white powder from t-butyl methyl ether.

REFERENCE EXAMPLE 1

A suspension of N-(2-methoxyethyl)-4-methylthio-3-nitrobenzamide (1.6 g) and palladium on charcoal (1.1 g; 5%) in ethyl acetate (60 ml) was shaken under an atmosphere of hydrogen at atmospheric pressure until hydrogen uptake ceased. The mixture was filtered and the residue was rinsed with ethyl acetate. The filtrate was concentrated in vacuo to leave N-(2-methoxyethyl)-4-methylthio-3-aminobenzamide (1.35 g) in the form of an oil that crystallised on standing, m.p. 66°-68° C. [Elemental analysis: C,54.8; H,6.69; N,11.5; S,12.9%; calculated: C,54.98; H,6.71; N,11.66; S,13.34%].

By proceeding in a similar manner but replacing the N-(2-methoxyethyl)-4-methylthio-3-nitrobenzamide by N-butyl-4-methylthio-3-nitrobenzamide there was prepared N-butyl-4-methylthio-3-aminobenzamide, m.p. 136°-137° C. [Elemental analysis: C,60.3; H,7.7; N,11.7; S,13.5%; calculated: C,60.50; H,7.56; N,11.76; S,13.45%].

By proceeding in a similar manner but replacing the N-(2-methoxyethyl)-4-methylthio-3-nitrobenzamide by N-(2-methylthioethyl)-4-methylthio-3-nitrobenzamide, and increasing the relative amount of catalyst, there was prepared N-(2-methylthioethyl)-4-methylthio-3-aminobenzamide, m.p. 80°-82° C. [Elemental analysis: C,51.4; H,6.34; N,10.8; S,25.1%; calculated: C,51.56; H,6.25; N,10.94; S,25.00%].

By proceeding in a similar manner but replacing the N-(2-methoxyethyl)-4-methylthio-3-nitrobenzamide by N-(2-methylthioethyl)-4-methoxy-3-nitrobenzamide there was prepared N-(2-methylthioethyl)-4-methoxy-3-aminobenzamide in the form of colorless crystals, m.p. 76°-77° C. [Elemental analysis: C,54.9; H,6.78; N,11.6; S,13.1%; calculated: C,54.97; H,6.71; N,11.65; S,13.34%].

REFERENCE EXAMPLE 2

A solution of 3-nitro-4-(methylthio)benzoic acid (2.5 g) in thionyl chloride (30 ml) was heated at reflux for 5 hours. Excess thionyl chloride was removed under reduced pressure. The residue of 3-nitro-4-(methylthio)benzoyl chloride, in dichloromethane (25 ml), was added over 10 minutes to a stirred solution of 2-methoxyethylamine (1.95 g) in dichloromethane (25 ml). The mixture was stirred for 1 hour and was then left overnight. Concentration in vacuo left an orange solid which was crystallized from a mixture of ethanol (40 ml) and water (25 ml) to give N-(2-methoxyethyl)-4-methylthio-3-nitrobenzamide (2.0 g) in the form of a yellow solid, m.p. 117°-118° C. [Elemental analysis: C,48.8; H,5.29; N,10.30; S,11.9%; calculated: C,48.88; H,5.22; N,10.36; S,11.86%].

By proceeding in a similar manner but replacing the 2-methoxyethylamine by butylamine there was prepared N-butyl-4-methylthio-3-nitrobenzamide in the form of a granular yellow solid, m.p. 125°-127° C. [Elemental analysis: C,53.4; H,6.0; N,10.4; S,12.0%; calculated: C,53.73; H,5.97; N,10.45; S,11.94%].

By proceeding in a similar manner but replacing the 2-methoxyethylamine by one equivalent of 2-methylthioethylamine plus 1.1 equivalents of triethylamine there was prepared N-(2-methylthioethyl)-4-methylthio-3-nitrobenzamide in the form of yellow needles after crystallization from aqueous propan-2-ol, m.p. 143°-145° C. [Elemental analysis: C,45.9; H,4.89; N,9.80; S,22.5%; calculated: C,46.15; H,4.90; N,9.80; S,22.37%].

By proceeding in a similar manner but replacing the 2-methoxyethylamine by one equivalent of 2-methylthioethylamine plus 1.2 equivalents of triethylamine and by replacing the 4-methylthio-3-nitrobenzoic acid by 4-methoxy-3-nitrobenzoic acid there was prepared N-(2-methylthioethyl)-4-methoxy-3-nitrobenzamide in the form of a brown powder after crystallization from aqueous ethanol and then from toluene, m.p. 81°-83° C. [Elemental analysis: C,48.8; H,5.1; N,10.2; S,11.7%; calculated: C,48.87; H,5.22; N,10.35; S,11.86%].

REFERENCE EXAMPLE 3

A solution of methyl 4-methylthio-3-nitrobenzoate (11.7 g) and sodium hydroxide (4.1 g) in ethanol (234 ml) and water (117 ml) was heated at reflux for 2 hours and was then concentrated in vacuo to about 70 ml. Water (250 ml) was added and the mixture was warmed to give a solution which was acidified with acetic acid (30 ml). The mixture was stirred while cooling and the resulting solid collected and washed with water to yield 4-methylthio-3-nitrobenzoic acid (10.3 g), m.p. 245°-247° C. [Elemental analysis: C,45.2; H,3.22; N,6.48; S,14.1%; calculated: C,45.07; H,3.29; N,6.57; S,15.02%].

REFERENCE EXAMPLE 4

Methyl 4-fluoro-3-nitrobenzoate (13.6 g) was added over 10 minutes to a stirred solution of sodium thiomethoxide (4.8 g) in 1,3-dimethyl-2-imidazolidinone (100 ml). The dark brown solution was stirred for 2 hours and was then heated on a steam bath for 2.5 hours. After cooling, the solution was poured into water (1.0 liter) and was extracted with diethyl ether (300 ml and then 2×200 ml). The ether solution was washed with water (2×250 ml), was dried over magnesium sulphate and was then concentrated in vacuo to leave an orange slurry. Crystallization from methanol provided methyl 4-methylthio-3-nitrobenzoate (3.45 g), m.p. 118°-120° C. [Elemental analysis: C,47.8; H,3.9; N,6.2; S,13.7%; calculated: C,47.58; H,3.96; N,6.17; S,14.1%].

REFERENCE EXAMPLE 4A

Methyl 4-methylthio-3-nitrobenzoate was also prepared in a similar manner to that in Reference Example 4 but using methyl 4-chloro-3-nitrobenzoate in place of the methyl 4-fluoro-3-nitrobenzoate and using acetone in place of the 1,3-dimethyl-2-imidazolidinone and without heating.

REFERENCE EXAMPLE 5

A solution of 4-(decylthio)bromobenzene (32.9 g) in dry tetrahydrofuran (100 ml) was added over about 30 minutes to a stirred, refluxing suspension of magnesium turnings (2.64 g) and one crystal of iodine in dry tetrahydrofuran (100 ml). The mixture was then stirred at reflux for 2 hours after which it was cooled to −70° C. Carbon dioxide was passed through the stirred solution at −70° C. for about 2 hours. The solution was warmed to room temperature and was then poured into a mixture of ice and water (1.25l). Hydrochloric acid was added to bring the pH to 1, the precipitate was collected and washed with water, dried and then crystallized from cyclohexane to yield 4-(decylthio)benzoic acid (20.29 g) in the form of white crystals, m.p. 108°-109° C. [Elemental analysis: C,69.2; H,8.9; S,11.1%; calculated: C,69.34; H,8.9; S,10.88%].

REFERENCE EXAMPLE 6

4-Bromothiophenol (100 g) was added dropwise to a solution of sodium methoxide prepared from sodium (13.4 g) and dry methanol (400 ml). The solution was stirred for 1 hour and then a mixture of 1-bromodecane (128.6 g) and dry methanol (150 ml) was added over 10 minutes. The oily suspension was refluxed for 4 hours and was then concentrated by distilling off about 300 ml of solvent. Water (750 ml) was added and the mixture was stirred vigorously while cooling. The solid product was collected, washed with water and then crystallized from ethanol to give 4-(decylthio)bromobenzene (159.5 g), m.p. 37°-39° C. [Elemental analysis: C,58.0; H,7.7; Br,24.5; S,9.7%; calculated: C,58.36; H,7.60; Br,24.31; S,9.73%].

The present invention also includes within its scope pharmaceutical formulations which comprise at least one of the compounds of formula I in association with a pharmaceutically acceptable carrier or coating. In clinical practice the compounds of the present invention may be administered parenterally, rectally or orally.

Solid compositions for oral administration include compressed tablets, pills, powders and granules. In such solid compositions, one or more of the active compounds is, or are, admixed with at least one inert diluent such as starch, sucrose or lactose. The compositions may also comprise, as is normal practice, additional substances other than inert diluents, e.g. lubricating agents, such as magnesium stearate.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting and suspending agents, and sweetening, flavoring, perfuming and preserving agents. The compositions according to the invention for oral administration also include capsules of absorbable material such as gelatin, containing one or more of the active substances with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. The compositions may also contain adjuvants such as stabilising, preserving, wetting, emulsifying and dispersing agents. They may be sterilized, for example, by filtration through a bacteria-retaining filter, by incorporation in the compositions of sterilising agents, by irradiation or by heating. They may also be manufactured in the form of sterile solid compositions, which can be dissolved in sterile water or some other sterile injectable medium immediately before use.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from 0.5 to 70, preferably 1 to 10, mg/kg body weight per day by oral administration.

The following Example illustrates pharmaceutical compositions according to the present invention.

Composition Example 1

No. 2 size gelatin capsules each containing:

| | |
|---|---|
| N-[2-methylthio-5-(2-methylthioethylamino-carbonyl)]phenyl-4-(decylthio)benzamide | 20 mg |
| lactose | 100 mg |
| starch | 60 mg |
| dextrin | 40 mg |
| magnesium stearate | 1 mg | were prepared in accordance with the usual procedure.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. A compound of the formula:

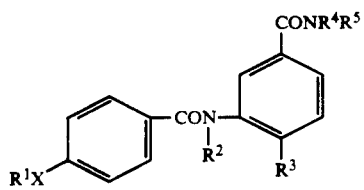

wherein
- $R^1$ is a straight- or branched-chain alkyl group containing from 4 to 18 carbon atoms, a straight- or branched-chain alkyl group containing from 4 to 18 carbon atoms with one or more carbon-carbon double or triple bonds, a straight- or branched-chain alkyl group containing from 4 to 18 carbon atoms interrupted by one or more hetero atoms, or a straight- or branched-chain alkyl group containing from 4 to 18 carbon atoms with one or more carbon-carbon double or triple bonds and interrupted by one or more hetero atoms;
- $R^2$ is hydrogen, methyl, or ethyl;
- $R^3$ is a halogen atom or a straight- or branched-chain alkyl group of 1 to 5 carbon atoms, or a group of the formula —OY or —SY, or is the dimethylamino group;
- $R^4$ and $R^5$ are each independently hydrogen, a straight- or branched-chain alkyl group of 1 to 6 carbon atoms, optionally containing one or more carbon-carbon double or triple bonds, or a group of formula —$(CH_2)_m$—Z, wherein:
  Z is a group of the formula —$OCH_3$, —$SCH_3$ or —$N(CH_3)_2$ or an alkanoylamino group containing 1 to 3 carbon atoms, and m is 2, 3, or 4;
- X is an oxygen atom or a group of formula —$OCH_2$—, —S—, —S—$CH_2$— or —$NR^6$—;
- $R^6$ is hydrogen, methyl, ethyl, or an acyl group; and
- Y is a straight- or branched-chain alkyl group of 1 to 4 carbon atoms.

2. A compound according to claim 1, wherein $R^1$ is a straight- or branched-chain alkyl or alkenyl group of 4 to 18 carbon atoms; $R^3$ is a straight- or branched-chain alkyl group of 1 to 5 carbon atoms, or a group of formula —OY or —SY, or is the dimethylamino group; $R^4$ and $R^5$ are as defined in claim 1 except that Z is other than alkanoylamino, and $R^2$, X, $R^6$ and Y are as defined in claim 1.

3. A compound according to claim 1, wherein the hetero atoms in the definition of $R^1$ are oxygen, sulphur or nitrogen.

4. A compound according to claim 1, wherein the halogen atom in the definition of $R^3$ is chlorine or fluorine.

5. A compound according to claim 1, wherein the acyl group represented by $R^6$ is an alkanoyl group of 2 to 4 carbon atoms optionally substituted by one or more halogen atoms.

6. A compound according to claim 1, wherein the compound exhibits at least one of the following features:
   (1) $R^1$ is an alkyl group of 5 to 16 carbon atoms;
   (2) $R^2$ is hydrogen;
   (3) $R^3$ is methoxy or methylthio;
   (4) $R^4$ is hydrogen;
   (5) $R^5$ is either:
      (i) an alkyl group of 1 to 5 carbon atoms; or
      (ii) a group of formula —$(CH_2)_m$—Z, wherein m is 2 or 3 and Z is a methoxy or methylthio group; and/or
   (6) X is an oxygen or sulphur atom; the other symbols being as defined in claim 1.

7. A compound according to claim 1, wherein the compound is:
   N-[2-methylthio-5-(2-methoxyethylaminocarbonyl)]-phenyl-4-decyloxybenzamide;
   N-(2-methylthio-5-butylaminocarbonyl)phenyl-4-decyloxybenzamide;
   N-[2-methylthio-5-(2-methylthioethylaminocarbonyl)]phenyl-4-decyloxybenzamide;
   N-[2-methylthio-5-(2-methylthioethylaminocarbonyl)]phenyl-4-(decylthio)benzamide;
   N-[2-methoxy-5-(2-methylthioethylaminocarbonyl)]-phenyl-4-decyloxybenzamide;
   N-[2-methoxy-5-(2-methylthioethylaminocarbonyl)]-phenyl-4-nonyloxybenzamide;
   N-(2-methoxy-5-butylaminocarbonyl)phenyl-4-(decylthio)benzamide;
   N-butyl-4-methyl-3-[4-(3,6,9-trioxadecyloxybenzamido)]benzamide;
   3-[4-(N-decyl)trifluoroacetamido]benzamido-4-methoxy-N-(2-methylthioethyl)benzamide; or
   3-(4-decylaminobenzamido)-4-methoxy-N-(2-methylthioethyl)benzamide.

8. A pharmaceutical composition comprising a pharmaceutically effective amount of a compound as defined in claim 1 and a pharmaceutically acceptable diluent or carrier.

9. A method of inhibiting acyl coenzymeA:cholesterol-O-acyl transferase (ACAT), comprising administering a pharmaceutically effective amount of the composition of claim 8 to a mammal host to inhibit ACAT.

10. A method of treating atherosclerosis, hyperlipidemia, cholesterol ester storage disease and atheroma, comprising administering a pharmaceutically effective amount of the composition of claim 8 to a mammal host to inhibit ACAT.

* * * * *